(12) United States Patent
Chahrour (10) Patent No.: US 10,314,732 B2
(45) Date of Patent: Jun. 11, 2019

(54) POSTURE PERFORMANCE GARMENT

(71) Applicant: ADRENALEASE INC., Toronto (CA)

(72) Inventor: Noureddin Chahrour, Toronto (CA)

(73) Assignee: Adrenalease Inc., Toronto, Ontario (CA)

(*) Notice: Subject to any disclaimer, the term of this patent is extended or adjusted under 35 U.S.C. 154(b) by 160 days.

(21) Appl. No.: 15/500,739

(22) PCT Filed: Jul. 31, 2015

(86) PCT No.: PCT/CA2015/050726
§ 371 (c)(1),
(2) Date: Jan. 31, 2017

(87) PCT Pub. No.: WO2016/019457
PCT Pub. Date: Feb. 11, 2016

(65) Prior Publication Data
US 2017/0216077 A1    Aug. 3, 2017

Related U.S. Application Data (60) Provisional application No. 62/032,199, filed on Aug. 1, 2014.

(51) Int. Cl.
*A61F 5/02* (2006.01)
*A41B 1/08* (2006.01)
(Continued)

(52) U.S. Cl.
CPC ............... *A61F 5/026* (2013.01); *A41B 1/08* (2013.01); *A41D 13/0015* (2013.01);
(Continued)

(58) Field of Classification Search
CPC .............................. A61F 5/026; A61F 5/3746
See application file for complete search history.

(56) References Cited

U.S. PATENT DOCUMENTS 3,856,004 A * 12/1974 Cox .................... A61F 5/05808
128/DIG. 19
4,785,803 A   11/1988 Benckhuijsen
(Continued)

FOREIGN PATENT DOCUMENTS

CN    2336766 Y    9/1999
EP    1398010 A1   3/2004
(Continued)

OTHER PUBLICATIONS

International Search Report and Written Opinion dated Oct. 30, 2015 in corresponding International Patent Application No. PCT/CA2015/050726.
(Continued)

*Primary Examiner* — Tajash D Patel
(74) *Attorney, Agent, or Firm* — Tony Orsi; Bereskin & Parr LLP/S.E.N.C.R.L., s.r.l.

(57) ABSTRACT

Various embodiments are described herein for a garment for improving an individual's posture when the individual wears the garment. The garment may comprise front and rear garment portions to cover at least a front portion and a rear portion respectively of the individual's torso. The garment also includes an adjustable set of straps that are adjustable from a rest position to a tensioned position and are collectively disposed over shoulder regions and under armpit regions of the front and rear garment portions. When the individual wears the garment and adjusts the straps to the tensioned position, the straps exert a downward retraction pulling force on the individual's shoulders and a backward pulling force on the individual's chest region thereby improving the individual's posture.

22 Claims, 7 Drawing Sheets

(51) Int. Cl.
*A41D 13/00* (2006.01)
*A61H 1/02* (2006.01)

(52) U.S. Cl.
CPC .............. *A61F 5/024* (2013.01); *A61F 5/028* (2013.01); *A61H 1/0292* (2013.01); *A41D 2400/32* (2013.01); *A61H 2205/081* (2013.01)

(56) References Cited

U.S. PATENT DOCUMENTS

| | | |
|---|---|---|
| 6,440,094 B1 | 8/2002 | Maas |
| 7,134,969 B2 | 11/2006 | Citron et al. |
| 7,871,388 B2 | 1/2011 | Brown |
| 8,047,893 B2 | 11/2011 | Fenske |
| 8,083,693 B1 | 12/2011 | McKeon et al. |
| 8,932,236 B1 | 1/2015 | McKeon et al. |
| 2005/0197607 A1 | 9/2005 | Brown |
| 2007/0016120 A1 | 1/2007 | Latronica et al. |
| 2009/0062704 A1 | 3/2009 | Brown et al. |
| 2012/0059297 A1 | 3/2012 | Newkirk |
| 2014/0174454 A1* | 6/2014 | Naef ............... A61F 5/3723 128/845 |
| 2015/0040286 A1 | 2/2015 | Schultz et al. |
| 2015/0148727 A1* | 5/2015 | Collier ............ A61F 5/026 602/19 |

FOREIGN PATENT DOCUMENTS

| | | |
|---|---|---|
| WO | 2013/138468 A1 | 9/2013 |
| WO | 2016019457 A1 | 2/2016 |

OTHER PUBLICATIONS

Extended European Search Report dated Mar. 26, 2018 in corresponding European Patent Application No. 15830270.3.

\* cited by examiner

POSTURE PERFORMANCE GARMENT

FIELD

Various embodiments are described herein for garments that improve the posture of the person wearing the garment.

BACKGROUND

Musculoskeletal disorders or (MSD) are forms of injuries affecting connective tissue such as muscles, nerves, joints, cartilage and spinal discs (Bureau of Labor Statistics, 2008). Some estimates state that 70% of all people will experience neck and shoulder pain though out their lives due to sedentary behavior and Work Related Musculoskeletal Disorders (WMSD). This pain occurs in individuals who hold certain postures for prolonged periods of time which in turn affects their neck and shoulder muscles as there is too much tension on these muscle groups. These injuries may occur when muscles or tendons are either over-used or stretched past their capabilities. Ergonomic risk factors such as repetitive motion, awkward posture, forceful exertions, pressure points, and static postures can cause or worsen MSD (NIOSH, 2007). For example, repetitive strain injury (such as carpal tunnel syndrome, and tendinitis) of the wrist and arm have risen by 80% since 1990 according to the US bureau of Statistics, and are now the single largest cause of work related injury. This is being described as the epidemic of the nineties. In the US alone, more than 600,000 workers have MSD resulting in days away from work each year (Bureau of Labor Statistics, U.S. Department of Labor, (2001). MSDs impact Canadian society by costing the health care system $20 billion (McGee et al., 2007).

Long periods of using a computer at work settings have been shown to cause musculoskeletal discomfort and mood disturbances; however, active or passive stretches have been shown to decrease the incidence of such disturbances (Sundelin et al. 1986, Zwahlen and Adams 1987, Swanson et al. 1989, Carter and Banister 1994, Hales et al. 1994). Frequent stretches can also reduce static loads on the musculoskeletal system including the muscles and the spine (Sundelin and Hagberg 1989).

Electromyographic studies were conducted by Anderson (1984) to measure muscle activation in a set of office workers using surface electrodes which were placed strategically on various muscles in the neck/shoulder and back. Results demonstrated that certain muscles, like the upper trapezius muscle, were highly activated during 90 degree elevation of the shoulder joint (Anderson, 1984). A possible reason for this could be that computer workers postures are poor due to slouching over their computers with elevation of the arms due to typing on the keyboard all day. This may result in specific back muscles being overly activated and reaching peak force when constantly stimulated. Active or passive stretching may lower the peak force and rate of firing and therefore take pressure away from these muscles.

Stretching, whether active or passive, is a form of physical activity in which skeletal muscles are lengthened to improve muscles elasticity and reduce tensile stress (Knudson et al. 2000; Harvey et al., 2002; Shrier, 2004; Decoster et al., 2005). The benefits of stretching include increased flexibility, improved range of motion within joints, improved circulation improved posture, and stress relief (Magnusson and Renstrom, 1998). In biomechanics terms, flexibility is the ability to change muscle tendon length which is brought about by viscoelastic properties (Sharman, Melanie, Cresswell, Riek. 2006). Viscoelasticity is a measure of a tissue's ability to deform or change length when a load is applied to it over time and to resume its original size and shape when the force is removed, much like stretching and releasing a rubber band (Sharman et al., 2006).

Active or passive stretching increases the distance a tissue can stretch as well as the force required to tear the muscle tendon unit, making injury less likely. The presumption is that, for individuals with short or "tight" muscles, stretching increases flexibility by elongating muscle fibers to a more physiologically normal range, promoting optimal function and reducing the risk of musculoskeletal injury.

Several research studies have shown that stretching as mentioned results in elongation of the muscle tendon unit, as well as reductions in peak force and rate of force production, therefore making the muscle tendon less stiff (Knudson et al., 2000; Harvey et al. 2002; Guissard and Duchateau, 2004; Decoster et al. 2005). This increases the distance a tissue can stretch as well as the force required to tear it; thus onset of injury is reduced. The presumption is that if muscles are tight (i.e. shorter in length) then chances of injury may increase. In fact, most sedentary individuals that have tight muscles suffer from pain in the neck and shoulder region due to not stretching their neck and shoulder muscles.

A study by the National Institute of Occupational Safety and Health (NIOSH) and the Internal Revenue Service (IRS) examined the symptoms and performance of data-entry workers. Participants from the Cincinnati IRS Service Center were sampled for analyses. The data sample included 47 women and 4 men, aged 23-60 years, with a mean age of 36 years. Data-entry experience ranged from 1 month to 24 years, with a mean of 6 years. One group had rest breaks along with stretch exercise breaks and the control group did not do either. The stretch exercise breaks were organized as follows: 4 weeks (two 15 min breaks/day); 4 weeks with supplementary breaks (two 15 min breaks plus four 5 min breaks/day). A questionnaire was then filled out by both groups of workers and it was reported that the workers in the rest/exercise break group only participated in 25% of conventional rest breaks and 39% of supplementary stretch exercise breaks. The study did not find any major conclusion of stretching and discomfort or performance. This was due to low compliance and low participation rates to perform the stretches as mentioned by Galinsky, Swanson, Sauter, Dunkin, Hurrell, & Schleifer, (2007). This low compliance may be attributed to a lack of motivation to do the stretches actively. However the individuals who did perform the stretches had lower discomfort and lower eyestrain during their work sessions. Also, the efficiency of these workers was significantly faster in data-entry speed at work and they made up for the 20 minute breaks by producing better output. Trujillo & Zeng (2006) from East Carolina University observed the effectiveness of a computer-based stretch program that notified the computer user to stop and stretch in the hope of offsetting musculoskeletal disorders. The computer-based stretch program demonstrated that the stretches helped relax tense muscles, improve blood circulation, increase the person's Range of Motion (ROM) and prevent cumulative trauma disorders.

There have been efforts to reduce the risk factors for MSD including ergonomic engineering and active stretch programs but the compliance rate and participation rate, as research indicates, is very low most commonly due to a lack of motivation.

SUMMARY OF VARIOUS EMBODIMENTS

In a broad aspect, at least one embodiment described herein provides a garment for improving an individual's posture when the individual wears the garment, wherein the garment comprises a front garment portion to cover at least a front portion of the individual's torso; a rear garment portion to cover at least a rear portion of the individual's torso, the rear garment portion being attached to the front garment portion; and an adjustable set of straps that are adjustable from a rest position to a tensioned position, the straps collectively being disposed over shoulder regions and under armpit regions of the front and rear garment portions, wherein, when the individual wears the garment and adjusts the straps to the tensioned position, the straps exert a pulling force on the individual's shoulders and chest region thereby improving the individual's posture.

In at least some embodiments, the straps may exert a downward retraction pulling force on the individual's shoulders and a backward pulling force on the individual's chest region when in the tensioned position.

In at least some embodiments, the set of straps may comprise anchored portions that are anchored to the rear garment portion and the end portions of the straps extend to the front garment portion.

In at least some embodiments, during use in the tensioned position, end portions of straps that extend over the shoulder regions may be releasably coupled to end portions of straps that extend under the armpit regions and the releasably coupled end portions are disposed along an area of the front garment portion.

In at least some embodiments, the front and rear garment portions may comprise sleeves that house the adjustable straps and have openings through which the end portions of the straps extend during use.

In these embodiments, during use the end portions of the straps retract within the openings when the straps are in the rest position.

In these embodiments, the end portions of the straps retract within the respective openings in the front garment portion so as not to be visible but can still be gripped when the individual reaches into the openings in the front garment portion.

In at least some embodiments, opposing end portions of the sleeves near the openings may be angled so that the opposing end portions of the straps form an arc in the tensioned position.

In at least some embodiments, a top set of sleeves that extend over the shoulder regions of the front and rear garment portions may be angled in a V pattern and may meet at a mid-region of a lower sleeve that extends under the armpit regions of the front and rear garment portions.

In at least some embodiments, a top set of sleeves that extend over the shoulder regions of the front and rear garment portions may approximately run vertically down to separate regions of a lower sleeve that extends under the armpit regions of the front and rear garment portions.

In at least some embodiments, the sleeves may be formed by continuous sheets of material.

Alternatively, in at least some embodiments, the sleeves may be formed by a series of loops.

In at least some embodiments, in the tensioned position, opposing end portions of the straps may releasably couple to one another.

Alternatively, in at least some embodiments, in the tensioned position, end portions of the strap may releasably couple to regions on the front garment portion.

For example, in the tensioned position, end portions of the strap that extend over the shoulder regions of the garment may releasably couple to an upper region on the chest area of the front garment portion and the end portions of the straps that extend under the armpit regions may releasably couple to a lower chest region on the front garment.

In at least some embodiments, end portions of the straps may be at least one of thicker and wider when the individual has a larger torso.

In at least some embodiments, the anchored portions of the straps may be anchored on separate areas of the rear garment portion.

In at least some embodiments, the straps may be resilient.

In another broad aspect, at least one embodiment described herein provides a garment for altering the posture of an individual, comprising an adjustable set of straps, encircling the back and shoulders of the individual, the straps have ends which can be adjustably connected at a point adjacent to the front of the shoulders of an individual wearing the garment, the adjustment of the straps allowing the tension of the straps to be varied to bias the shoulders of individual back and downward from a non-tensioned, rest position.

In at least some embodiments, the straps may be received in sleeves on the garment, the ends of the straps extending beyond the sleeves.

In at least some embodiments, the sleeves may comprise a series of loops, fastened to the garment, through which the straps are located.

In at least some embodiments, the sleeves may comprise fabric passages formed in the garment.

In at least some embodiments, the straps may be resilient.

In another broad aspect, at least one embodiment described herein provides a method for making a posture garment for improving an individual's posture when the individual wears the garment, wherein the method may comprise: forming front and rear garment portions of the posture garment; anchoring first end portions of upper straps and a portion of a lower strap to anchor points near a midline region of the rear garment portion; mounting sleeves over the straps and attaching the sleeves on the posture garment while leaving openings near upper shoulder regions and beneath armpit regions where the rear garment portion will be attached to the front garment portion; attaching the front garment portion and the rear garment portion to one another; and providing end portions of the straps with attachment means.

In another broad aspect, at least one embodiment described herein provides a garment for applying a passive stretch to an individual's upper body when the individual wears the garment, wherein the garment may comprise a front garment portion to cover at least a front portion of the individual's torso; a rear garment portion to cover at least a rear portion of the individual's torso, the rear garment portion being attached to the front garment portion; and an adjustable strap mechanism that comprises a set of straps extending above shoulder regions and below armpit regions of the garment from the rear garment portion to the front garment portion, the adjustable strap mechanism being adjustable from a rest position, where the straps are disengaged and no pulling force is applied to the garment wearer, to a retracted position where the straps are engaged and a pulling force is applied to the garment wearer.

In at least some embodiments, the set of straps may be housed within a set of sleeves and in the rest position end portions of the straps may retract within the sleeves and in the retracted position, the end portions of the straps may engage one another or regions of the front garment portion.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Further aspects and features of the example embodiments described herein will appear from the following description taken together with the accompanying drawings.

DETAILED DESCRIPTION OF THE EMBODIMENTS

Various garments or methods will be described below to provide an example of at least one embodiment of the claimed subject matter. No embodiment described herein limits any claimed subject matter and any claimed subject matter may cover garments or methods that differ from those described herein. The claimed subject matter is not limited to garments or methods having all of the features of any one process or device described below or to features common to multiple or all of the garments or methods described herein. It is possible that a garment or method described herein is not an embodiment of any claimed subject matter. Any subject matter that is disclosed in a system, device or method described herein that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 10%, for example.

At least one of the example embodiments of the garments or methods described in accordance with the teachings herein may be used to address issues related to MSD and are not dependent upon the motivation of the user (a.k.a. garment wearer) for success.

The present garments described in accordance with the teachings herein generally provide a passive stretch to certain muscles in at least one of the neck/shoulder, chest (pectoralis minor) and back regions of the garment wearer (e.g. the individual who is wearing the garment) depending on the amount of tension selected by the garment wearer, which tends to shorten the pectoralis minor and serratus anterior muscles during a prolonged protracted sitting posture or during "slouching". This provides the person wearing it the garment with the comfort of retracting his/her scapulas as well as his/her shoulders back into a retracted position, which is a healthy position for a posture. The individual wearing the garment has the ability to control and adjust the pulling force provided by using straps that are strategically placed along the shoulders, back regions along both scapulas and right underneath the armpit regions of the garment during use.

The adjustability of the straps of the garments described herein uniquely provides a passive stretch to at least one of the neck, upper back and shoulder muscles of the garment wearer depending on how tightly the straps are adjusted. The end portions of the adjustable straps are located near the shoulders of the garment wearer to make it easier for the garment wearer to grab the straps, and fasten them as desired to apply tension with the straps thereby pulling the garment wearer's shoulders back when needed and then releasing or de-tensioning the straps after a given period of time so that no pulling force is exerted on the garment wearer by the garment. The garment wearer may tension the straps for a given period of time to take pressure off of their neck and shoulder muscles when they are sedentary and/or slouched over for long periods of time (e.g. slouched over a computer all day or in other undesired positions for a long period of time) in which case the straps act as passive stretch mechanisms. Therefore, during use, the garment wearer may adjust the straps to experience a slight pull on their shoulders and a retraction of their scapulas placing them in a healthy postural position while providing a passive gentle stretch.

Conventional posture braces and posture shirts in the marketplace today pull the individual's back into the retracted position and hold them in that position for as long as they are wearing the garment. This may in fact worsen the individual's posture in the long term because the individual is relying on the posture garment to hold them back in that position all day, which effectively shuts off the individual's muscles and weakens them in the long run and worsens posture. No conventional posture garment has adjustable straps as are provided in the garments described in accordance with the teachings herein.

In other conventional garments that use straps to apply a pulling force on the individual's back, including posture shirts, braces, bras, brassieres, etc., only apply a small pull on the shoulders and the back of the individual wearing the garment to give the wearer a reminder to pull their shoulders back or hold the shoulders in that position for as long as he/she is wearing the garment.

In either of these aspects of the conventional garments, unless the individual must take off their posture garment and put it back on every time they feel discomfort in the neck and shoulder region and they will rely on the posture garment to do all the work for them. This is not ideal as the individual will not prefer to take the garment off and put it back on every time they feel discomfort in the neck and shoulder regions. Thus, the individual will tend to either not use these conventional garments, or will wear them for periods of time extending past the time when they should have removed the garments.

In contrast, with the various posture garments described in accordance with the teachings herein, the individual wearing the garment can easily and simply adjust the straps to relieve stress and pain on the neck and shoulder area by applying the passive stretch whenever they feel the need to do so. This means the individual wearing the garment, in accordance with the present teachings herein, does not need to take the garment off and put it back on when they need muscle relief as the straps can easily be released (a.k.a. de-strapped or de-tensioned) which allows the individual to go back to their normal posture therefore activating their muscles once again.

In another aspect, the posture garments described in accordance with the teachings herein allow the individual wearing the posture garment to adjust the amount of pulling force that is provided by the straps to maintain the garment wearer with the correct posture or with a desired amount of passive stretching. The garment wearer can therefore track whether their posture has been improving with time, as they can compare the amount of adjustment that is needed by the straps in order to maintain the garment wearer's correct posture. It should be noted that over time, the garment wearer's muscles will be more accustomed to maintaining the correct posture on their own and not as much pulling force may be required by the straps. This is in contrast with conventional posture garments which simply apply the same amount of tension or pulling force to the garment wearer at all times.

In another aspect, at least one of the posture garments described in accordance with the teachings herein allow the garment wearer, as described in more detail below, to remove the adjustable straps from the posture garment to replace the straps with another set of straps that have a different thickness and width. The thicker and/or wider the straps, the more tensile pull that is offered by the straps to the shoulders and upper back regions of the garment wearer. Since these straps are resilient (e.g. stretchy), the wider they are, the more tensile pulling force they provide to the garment wearer. Furthermore, a posture garment with adjustable straps that are replaceable means that they can be changed at any time and/or removed for washing or cleaning of the garment.

In another aspect, at least one of the posture garments described in accordance with the teachings herein may have the ability to potentially enhance athletic performance of athletes who wear the posture garment as the posture garment may be used to place the individual wearing it into a retracted posture wherein their scapulas are pulled back and together towards the midline of their anatomical body which in turn pulls the shoulders back and opens up the thoracic region (i.e. chest region) allowing easier flow of breathing (i.e. inspiration and expiration) which may help increase aerobic performance. This passive stretch offered by the straps on the posture garment may also allow for more blood flow to go to the athlete's skeletal muscles that are exerting energy rather than the muscles that help with breathing (i.e. respiratory muscles), which may provide the athlete with more power and quickness.

In another aspect, at least one of the posture garments described in accordance with the teachings herein may employ straps that elastically retract when not used. These straps may be referred to as reflex elastic straps. In at feast some embodiments, the straps may retract into openings in the posture garment so that the straps are not visible when they are not used to apply a pulling or retracting force to adjust the posture of the garment wearer.

Figure 1A:
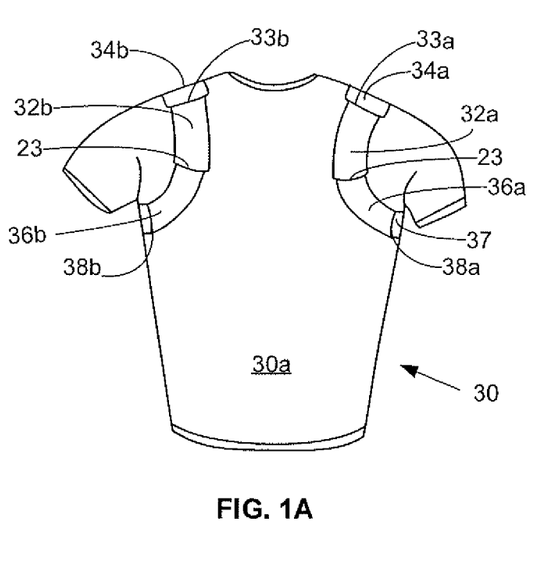
FIG. 1A is a front view of an example embodiment of a posture garment in accordance with the teachings herein.
Figure 1B:
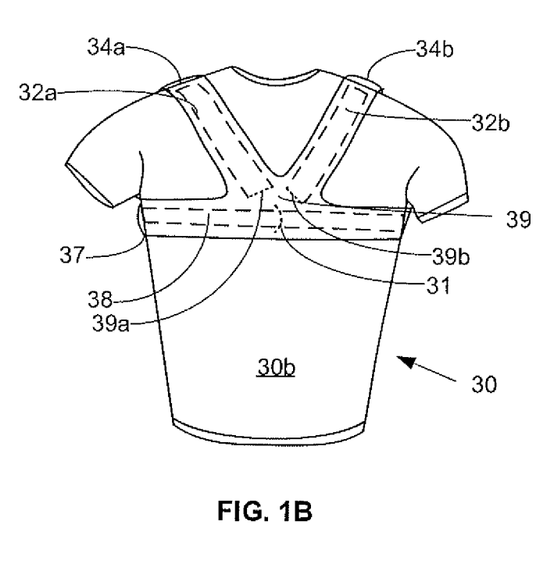
FIG. 1B is a rear view of the posture garment of FIG. 1A.

Referring now to FIGS. 1A and 1B, shown therein are front and rear views, respectively, of an example embodiment of a posture garment 30 for improving an individual's posture when the individual wears the garment in accordance with the teachings herein. The garment 30 includes a front garment portion 30a for covering at least a front portion of an individual's torso and a rear garment portion 30b that covers at least a rear portion of the individual's torso, when the individual is wearing the posture garment 30 during use. The the rear garment portion 30b may be attached to the front garment portion 30a using different techniques such as, but not limited to stitching, for example.

Figure 2B:
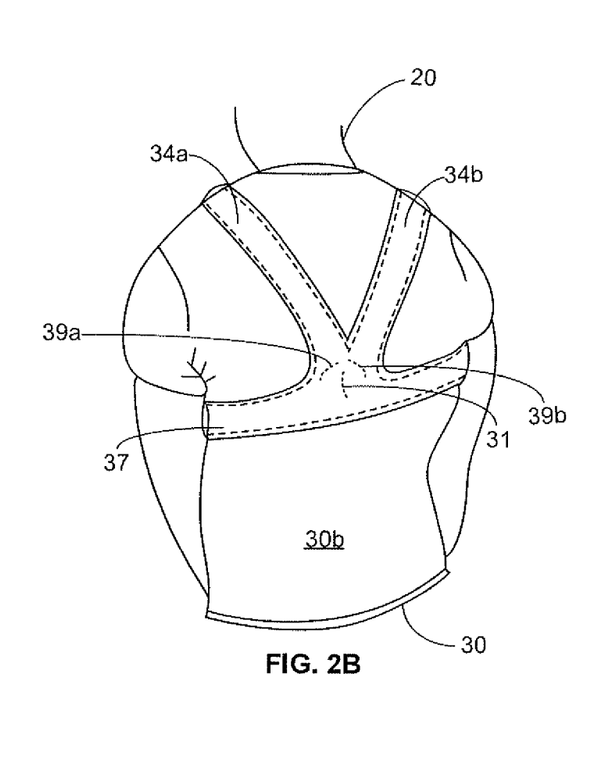
FIG. 2B is a rear view of the posture garment of FIG. 1A being worn by a user.
Figure 3A:
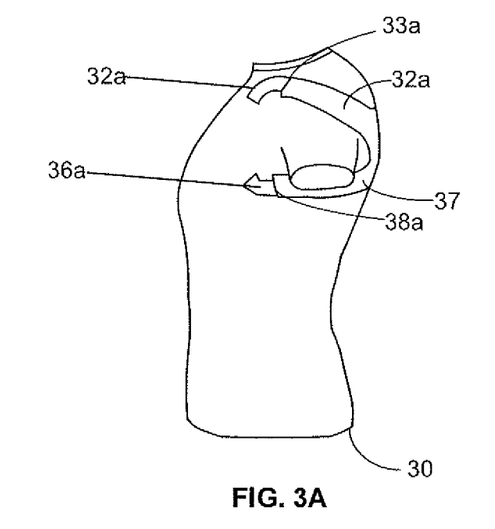
FIG. 3A is a side view of the posture garment of FIG. 1A with the garment in a relaxed position.
Figure 3B:
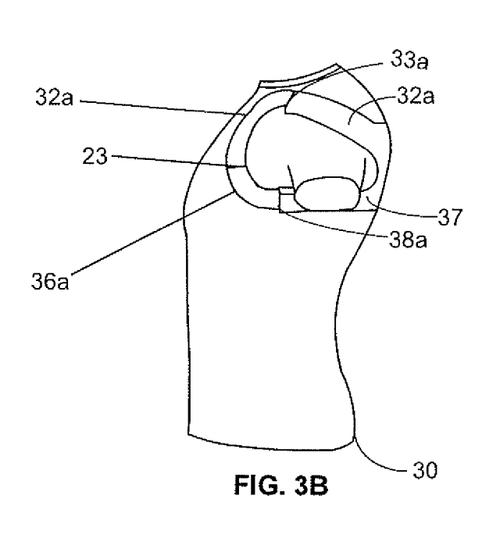
FIG. 3B is a side view of the posture garment of FIG. 1A with the garment in a retracted position.

The posture garment 30 also includes an adjustable strap mechanism that comprises a set of straps 32a, 32b and 36 having anchored portions 39a, 39b and 31, respectively, that are anchored to the posture garment 30 and end portions that are adjustable from a rest position (see FIG. 3A for example) to a tensioned or retracted position (see FIG. 3B for example). The straps 32a, 32b and 36 are collectively disposed over shoulder regions and under the armpit regions of the front and rear garment portions 30a and 30b. The straps 32a, 32b and 36 encircle the back and shoulders of the individual when worn by the individual. It should be noted that FIG. 1B shows the straps 32a, 32b and 36 whereas the other FIGS. 2B, 6A, 6B and 7 shows the stitching of the sleeves 34a, 34b and 37. It should be noted that there may be some embodiments where strap 37 is provided by two straps: a left strap and a right strap (not shown).

Accordingly, the adjustable strap mechanism comprises the set of straps 32a, 32b, and 36 extending above shoulder regions and below armpit regions of the garment 30 from the rear garment portion 30b to the front garment portion 30a. The adjustable strap mechanism is adjustable from a rest position, where the straps are disengaged and no pulling force is applied to the garment wearer, to a retracted position where the straps are engaged and a pulling force is applied to the garment wearer.

The straps 32a and 32b are upper straps and the strap 36 is a lower strap. The upper straps 32a and 32b are shown extending from openings 33a and 33b formed in respective sleeves 34a and 34b, while the lower strap 36 has two end portions 36a and 36b that extend from openings 38a and 38b from sleeve 37. Accordingly, the straps 32a, 32b and 36 are received in the respective sleeves 34a, 34b and 37 on the garment 30, and the ends of the straps 32a, 32b and 36 respectively extend beyond the sleeves 34a, 34b and 37. The sleeves 34a, 34b and 37 may also be referred to as channels or passages. In the illustrated example embodiment, the sleeves 34a, 34b and 37 retain straps 32a, 32b and 36, respectively, in place on the posture garment 30. As indicated the sleeves 34a, 34b and 37 may be sewn all around the garment 30 except for the openings 33a, 33b, 38a and 38b in the front portion 30a of the garment 30 where the straps 32a, 32b and 36 are coming out from. Accordingly, the front and rear garment portions 30a and 30b comprise the sleeves 34a, 34b and 37 that house the adjustable straps 32a, 32b and 36 and have openings 33a, 33b, 38a and 38b through which the end portions of the straps 32a, 32b and 36 extend during use.

In other embodiments, the position of the openings 33a, 33b, 38a and 38b may be different and may be at a region of the front garment portion 30a that is closer to the rear garment portion 30b or the openings 33a, 33b, 38a and 38b may be on a region of the rear garment portion 30b that is closer to the front garment portion 30b. Accordingly, various positions for the openings 33a, 33b, 38a and 38b may be used as long as the garment wearer is able to grip the ends of the straps 32a, 32b and 36 that come out of the openings 33a, 33b, 38a and 38b.

As indicated in the example embodiment, the sleeves 34a, 34b and 37 may be sewn or otherwise attached all around an upper portion of the rear garment portion 30b and possibly a small portion of the front garment portion 30a except for the openings 33a, 33b, 38a and 38b from which end portions for the straps 32a, 32b and 36 extend. Accordingly, the straps 32a, 32b and 38 are mostly covered by a covering panel of the sleeves 34a, 34b and 38, respectively.

During use, in the rest position, the end portions of the straps 32a, 32b and 36 retract towards the openings 33a, 33b, 38a and 38b, respectively. In at least some embodiments, the end portions of the straps 32a, 32b and 36 may retract within the openings 33a, 33b, 38a and 38b, respectively, when the straps 32a, 32b and 36 are in the rest position. In these embodiments, the end portions of the straps 32a, 32b and 36 may retract within the respective openings 33a, 33b, 38a and 38b in the front garment portion 30a so as not to be visible but such that they can still be gripped when the individual reaches into the openings 33a, 33b, 38a and 38b to place the straps 32a, 32b and 36 into the tensioned position.

During use, in the retracted or tensioned position, the end portions of the straps 32a, 32b and 36 can be adjustably and releasably connected at a point adjacent to the front of the shoulder regions of an individual wearing the posture garment 30. The adjustment of the straps 32a, 32b and 36 allow their tension (i.e. their amount of pulling or retracting force) to be varied to bias the shoulders of the individual wearing the garment back and downward by various amounts compared to the non-tensioned or rest position, thereby augmenting the posture of the individual wearing the posture garment 30.

In this example embodiment, the straps 32a, 32b and 36 are preferably each attached or anchored to the garment 30 at several distinct anchor points inside the sleeves 34a, 34b and 37 respectively. In this example embodiment, the straps 32a, and 32b are anchored to the sleeves 34a and 34b at anchor points 39a and 39b, respectively, while the strap 36 is anchored to the sleeve 37 at anchor point 31. Accordingly, the anchored portions of the straps 32a, 32b and 36 are anchored to the rear garment portion 30b and the end portions of the straps 32a, 32b and 36 extend to the front garment portion 30a in this example embodiment. The anchored portions of the straps 32a, 32b and 36 may be anchored on separate areas of the rear garment portion 30b.

In alternative embodiments, the straps 32a, 32b and 36 may be anchored at the same point such as the center region 39 between the sleeves 34a, 34b and 37. Accordingly, the straps 32a, 32b and 36 may be anchored to at least one point or region. In alternative embodiments, the straps 32a, 32b and 36 may be anchored to at least one point or region of the garment portion 30b instead of the sleeves 34a, 34b and 37.

In at least one embodiment, the straps 32a, 33a and 36 may be permanently attached to the sleeves 34a, 34b and 37, respectively, or at least one portion on the garment 30. Alternatively, the straps 32a, 33a and 36 may be removably or temporarily attached to the sleeves 34a, 34b and 37, respectively, or at least one portion on the garment 30 using various releasable fasteners such as, but not limited to, Velcro™, clips, suitable snap fasteners like buttons, and any other means of securing the straps 32a, 33a and 36, if desired. It should be noted that in some embodiments, the straps 32a, 32b and 36 will not be fastened to the posture garment 30 and will instead merely be held in place by sleeves 34a, 34b and 37.

The sleeves 34a, 34b and 37 may be provided in a variety of manners in different embodiments of the posture garment 30. For example, the sleeves 34a, 34b and 37 may be provided as enclosed sleeves (as illustrated) and formed using continuous sheets of material that may be solid or perforated. For example, the sleeves 34a, 34b and 37 may be fabric passages formed in the posture garment 30. Alternatively, the sleeves 34a, 34b and 37 may be provided as a series of loops (e.g. "belt loops") that are sewn or otherwise fastened to the portion garment 30 and through which the straps 32a, 32b and 37 are passed and located.

In the example embodiment shown in FIGS. 1A and 1B, the top set of sleeves 34a and 34b extend over the shoulder regions of the front and rear garment portions 30a and 30b, are angled in a V pattern on the rear garment portion and meet at a mid-region of the lower sleeve 37 that extends under the armpit regions of the front and rear garment portions 30a and 30b. The lower sleeve 37 may be at a mid-torso region in some cases.

In an alternative embodiment, the top set of sleeves 34a and 34b that extend over the shoulder regions of the front and rear garment portions 30a and 30b move approximately vertically down to separate regions of the lower sleeve 37 that extends under the armpit regions of the front and rear garment portions 30A and 30B.

In at least one of the example embodiments of the garment 30 described in accordance with the teachings herein, the straps 32a, 32b and 36 may be resilient and can be tensioned to increase their pulling force as desired by the garment wearer. This is further described in relation to FIGS. 3A and 3B.

As mentioned above, different widths or thicknesses may be used for the straps 32a, 32b and 36 to vary their resiliency as desired (in other words to vary the amount of tensile force that the straps may provide when engaged in the tensioned position). For example, 1.5 inch, 2 inch or 2.5 inch wide straps may be used as well as other sizes. Elastic materials with different tensile strengths may be used for the straps 32a, 32b and 36. In addition, there may be embodiments where the end portions of the straps 32a, 32b and 36 may be thicker when the individual has a larger torso as the increased thickness of the straps 32a, 32b and 36 may provide more tensile pull.

In alternative embodiments, different materials can be employed for the straps 32a, 32b and 36 to vary their resiliency. For example, the straps 32a, 32b and 36 may be made using one or more of elastic, spandex, polyspandex, or any material that is similar to kinesiotape and provides a tensile pull when stretched.

In general, the garment 30 may be made of various clothing materials including, but not limited to, at least one of cotton, polyester, spandex, nylon, lycra, bamboo, or any other suitable fabric.

When the individual wears the posture garment 30 and adjusts the straps 32a, 32b and 36 to the tensioned position, the straps 32a, 32b and 36 exert a downward pulling or retracting force on the individual's shoulders and a backward pulling force on the individual's chest region thereby improving the individual's posture.

Figure 2A:
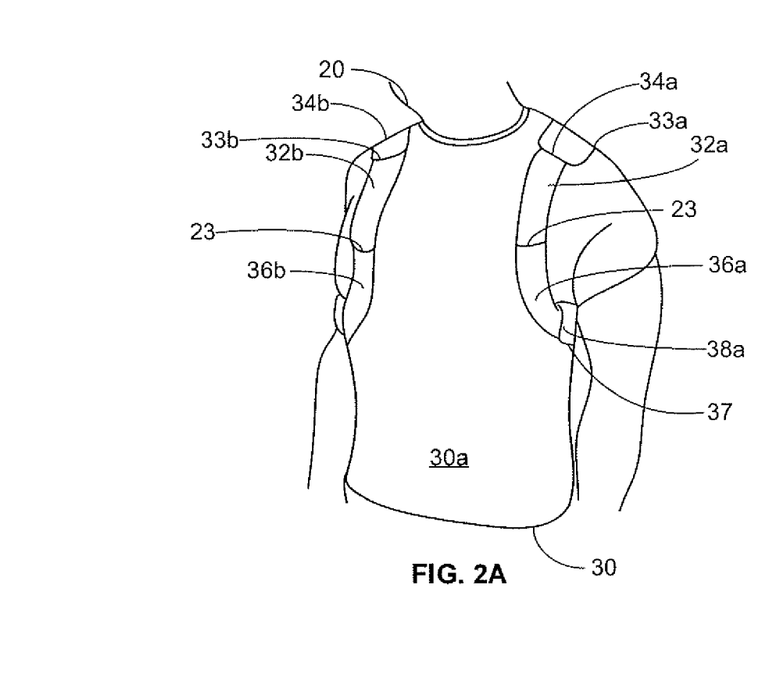
FIG. 2A is a front view of the posture garment of FIG. 1A being worn by a user.

Referring now to FIGS. 2A and 2B, shown therein are front and rear views, respectively, of the posture garment 30 when being worn by an individual 20. In the front or an anterior view of the posture garment 30 in FIG. 2A, the respective ends of the straps 32a, 32b and 36 come from the upper left side, the upper right side and the mid left and mid right sides of the posture garment 30. In this example embodiment, in the tensioned position, the end portions of the straps 32a and 32b extend over the shoulder regions of the garment 30 and are releasably coupled to end portions of the strap 36 that extends under the armpit regions of the posture garment 30 towards the front garment portion 30a. The end portions of the straps 32a, 32b and 36 can be seen to be coming out of the openings 33a, 33b, 38a and 38b which are located in between the posture garment 30 and the sleeves 34a, 34b and 37 respectively. The releasably coupled end portions of the straps 32a, 32b, and 36 are disposed along an area or region of the front garment portion 30a along an outer region of the pectoralis muscles of the individual 20. The respective ends of the straps 32a and 32b and the respective end portions 36a and 36b of the strap 36 may be releasably joined to one another at respective connection points 23, to tension the respective straps 32a, 32b and 36. Any suitable connector including, without limitation, Velcro™, D-Rings, snaps, connection clips, buttons, or any other suitable releasable connection means may be used to releasably and adjustably connect the respective ends of the straps 32a, 32b and 36. In the case of a Velcro™ connector, the "loop" portion of the Velcro™ may be fixed to one end of each of the respective straps 32a, 32b and 36 and the "hook" portion of the Velcro™ may be fixed to the other respective opposing end of each of the respective straps 32a, 32b and 36. Accordingly, in the tensioned position, opposing end portions of the straps 32a, 32b and 37 are releasably coupled to one another. In alternative embodiments, the opposing end portions of the straps 32a, 32b and 37 are releasably coupled to attachment regions on the front garment portion 30a.

When the end portions of the straps 32a, 32b and 36 are joined together at respective connection points 23, they will apply a pulling force to position the individual's 20 shoulders back and retract their scapulas, placing the individual 20 in a better postural position including possibly the correct postural position (depending on the amount of pulling force) and taking stress off of the neck, shoulder and back muscles of the individual 20. The individual 20 wearing the posture garment 30 has full control of the joining/connection of the straps 32a, 32b and 36 allowing the individual 20 to tension the straps to a desired amount, or de-tension them, while wearing the posture garment 30 as desired. The straps 32a, 32b and 36 can be easily adjusted by the individual 20 as the individual 20 may make the adjust where the connection points 23 occur on the respective ends of the straps 32a, 32b and 36 thereby making the connected straps 32a, 32b and 36 longer (to provide less tension) or shorter (to provide more tension) depending on how much tension they want the straps 32a, 32b and 36 to provide.

In the example embodiment of the posture garment 30, the opposing end portions of the sleeves 34a and 37 near the openings 33a and 38a are angled so that the opposing end portions of the straps 33a and 36 form an arc in the tensioned position. Likewise, the opposing end portions of the sleeves 34b and 37 near the openings 33b and 38b are angled so that the opposing end portions of the straps 33b and 36 form an arc in the tensioned position which may help to stabilize the scapulas and help in retracting them.

Referring now to FIGS. 3A and 3B, shown therein are side views of the posture garment 30 with the garment 30 in a relaxed or rest position and a retracted or tensioned position, respectively. In FIG. 3A, the straps 32a, 32b and 36 are not joined together and therefore there is no passive stretch acting on any muscle when the individual 20 is wearing the garment 30. It should be noted that FIG. 3A shows the end portions of the straps 32a, 32b and 36 extend past the openings 34a, 34b, 38a and 38b of the sleeves 33a, 33b and 37 in the rest position. However, in other embodiments, the end portions of the of the straps 32a, 32b and 36 may retract within the openings 34a, 34b, 38a and 38b of the sleeves 33a, 33b and 37 so that they are not visible in the rest position. In FIG. 3B, the end portions of the straps 32a, 32b and 36 are joined and will apply a pulling force to the shoulder and upper back regions of the individual 30 when they wear the garment 30 so that the joined straps 32a, 32b and 36 will retract the shoulders and upper back regions of the individual 30 to a retracted posture and provide a passive stretch. This passive stretch may, depending on the amount of force that is applied by the joined straps 32a, 32b and 36, open up the ribcage of the individual 30 which allows for easier breathing and reduces the burden or work that must be done by the respiratory muscles during inhalation and exhalation.

Figure 4A:
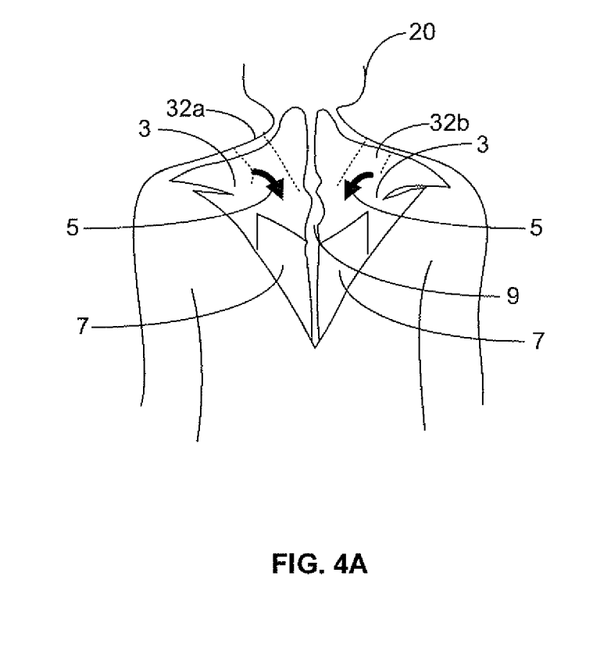
FIGS. 4A and 4B show the tension provided by the posture garment to the neck, shoulder and back regions of the garment wearer during use when the garment is in the retracted position.
Figure 4B:
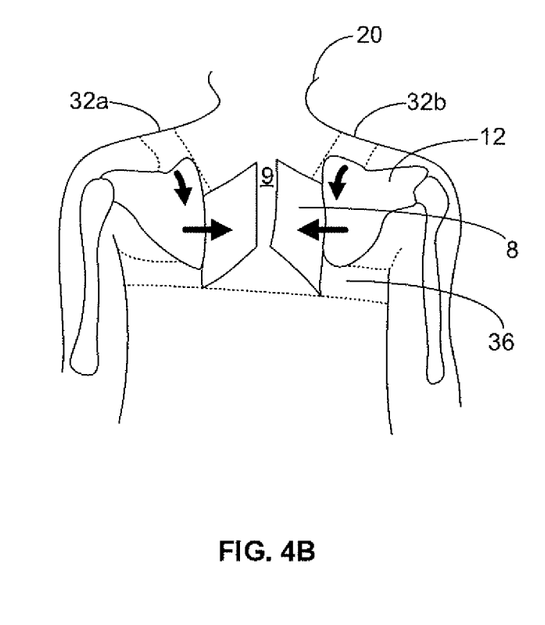

The various embodiments of the posture garment 30 described in accordance with the teachings herein differ from other posture braces and posture shirts/garments in that the straps 32a, 32b and 36 can be easily adjusted in seconds with a slight pull of the straps 32a, 32b and 36 near the shoulder and armpit regions of the garment 30. This allows the individual 20 to de-tension (or "de-strap") the straps 32a, 32b and 36 to return to their regular posture after a given period of time by de-tensioning or releasing the straps 32a, 32b and 36 into the de-strapped or rest position. Therefore, when the individual 20 feels discomfort in their neck and shoulder areas (e.g. due to tightness of muscles) they can re-join or reconnect the straps 32a, 32b and 36 together and apply tension as indicated in FIG. 3B to provide a passive stretch and relax those tense muscles for a certain period of time, such as about 10-15 minutes. This may be done every time the individual 20 feels that their neck and shoulder muscles are tight. The ability to join and release the straps 32a, 32b and 36 makes it easy for the individual 20 to keep the posture garment 30 on rather than taking it off when they don't need passive stretching and then putting it back on when they feel discomfort as they can connect the end portions of the straps 32a, 32b and 36 and un-connect them (i.e. de-strap) once the individual 20 feels that their neck and shoulder pain is relieved Referring now to FIGS. 4A and 4B, shown therein is the tension provided by the posture garment 30 to the neck, shoulder and back regions of the garment wearer 20 during use when the garment is in the retracted or tensioned position. In particular, FIG. 4A represents a posterior view of the muscles as well as sections of the straps 32a, 32b and 36. As can be seen, when tensioned, the straps 32a and 32b provide a downwards pull on the scapulas 12 as well as pulling the individual's shoulders 9 back. The straps 32a and 32b are also stretching certain muscles as shown in FIG. 4B such as the trapezium muscles 5, 3 and 7. Either side of the strap 36 provides a pull towards the midline of the individual's back 9 and pulls the muscles in this area into the retracted position such as the rhomboids 8 and the lower trapezium muscles 7.

Figure 5A:
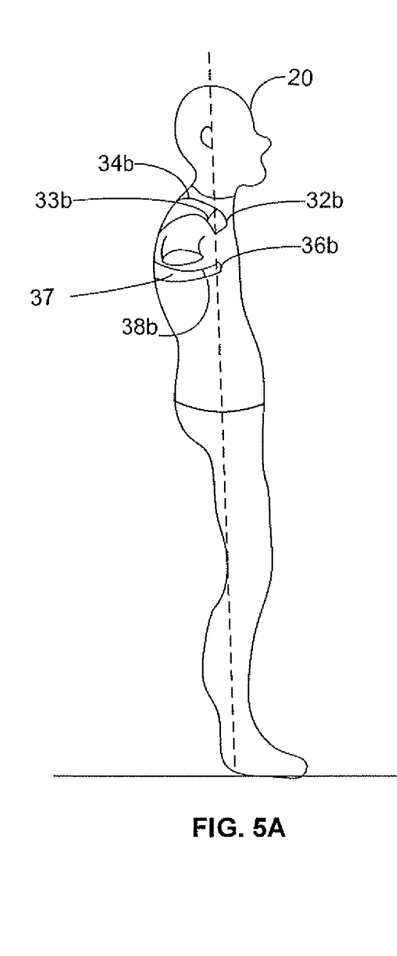
FIG. 5A is a side view of the garment wearer during use when the garment is in the relaxed position.
Figure 5B:
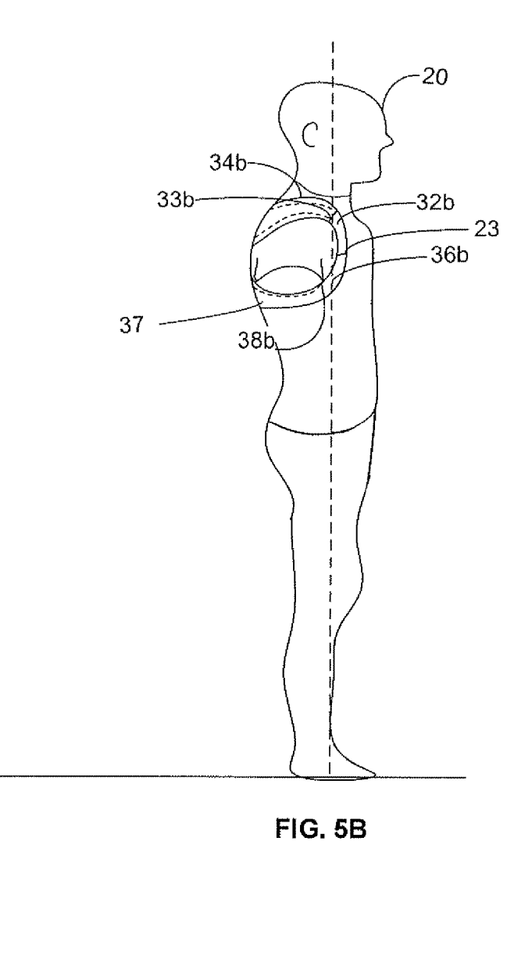
FIG. 5B is a side view of the garment wearer during use when the garment is in the retracted position.

Referring now to FIGS. 5A and 5B, shown therein are side views of the individual 20 wearing the posture garment 30 during use when the garment 30 is in the relaxed position and the retracted position, respectively. In FIG. 5A, the end portions of the straps 32a, 32b and 36 are not joined together at the connection points 23 and the individual 20 has poor posture. In FIG. 5B, the individual 20 wearing the posture garment 30 has the end portions of the straps 32a, 32b and 36 joined together at connection points 23 and the garment 30 is providing a passive stretch to the individual's shoulders and surrounding muscles which improves the individual's posture and also gives relief to the muscles in the individual's neck, shoulder and upper back areas.

Figure 6A:
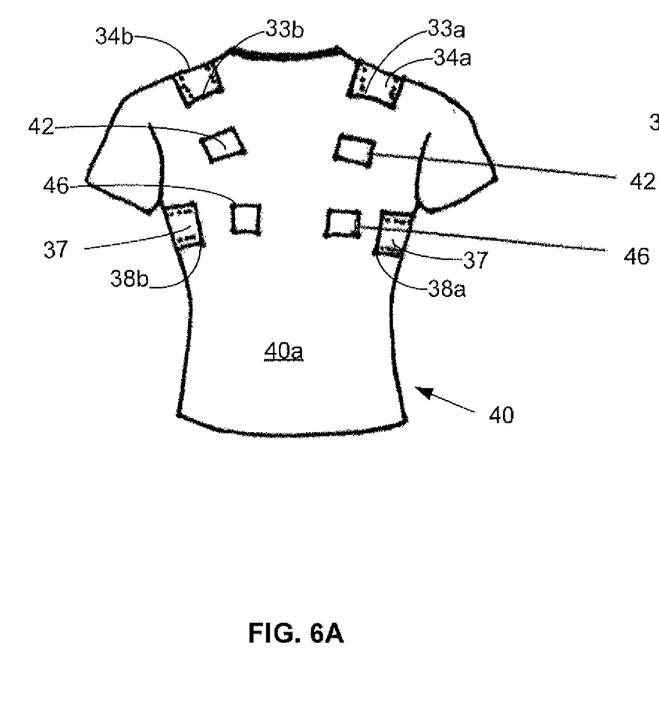
FIG. 6A is a front view of an alternative embodiment of a posture garment in the relaxed position.
Figure 6B:
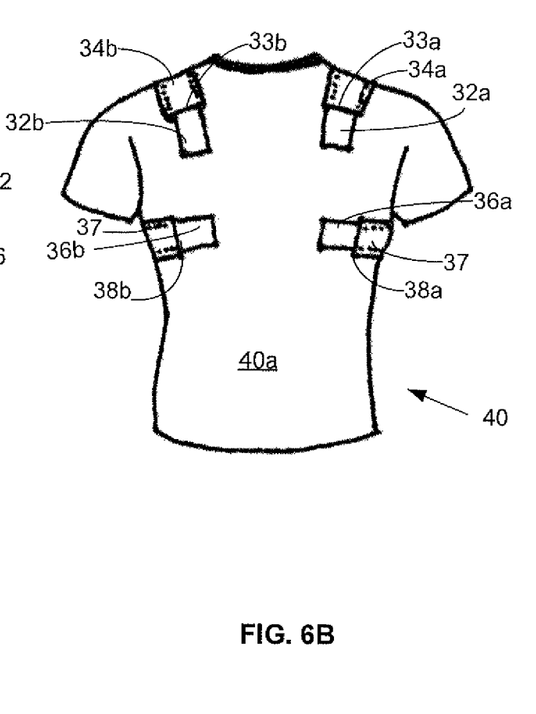
FIG. 6B is a front view of the posture garment of FIG. 6A when the posture garment is in the retracted position.

Referring now to FIGS. 6A and 6B shown therein are front views of an alternative embodiment of a posture garment 40 in the relaxed position and the retracted position, respectively. FIG. 6A, depicts the same straps 32a, 32b and 36. The same overall design for the sleeves that house the straps may also be used. However, in the tensioned position, the end portions of the straps 32a and 32b may be releasably attached onto the garment 40 at attachment regions 42 and the end portions of the strap 36 may be releasably attached onto the garment 40 at attachment regions 46. In particular, end portions of the straps 32a and 32b that extend over the shoulder regions of the posture garment 40 may releasably couple to an upper region on the chest area on the front garment portion 40a and the end portions 36a and 36b of the strap 36 that extend under the armpit regions of the posture garment may releasably couple to a lower chest region on the front garment portion 40a.

Figure 7:
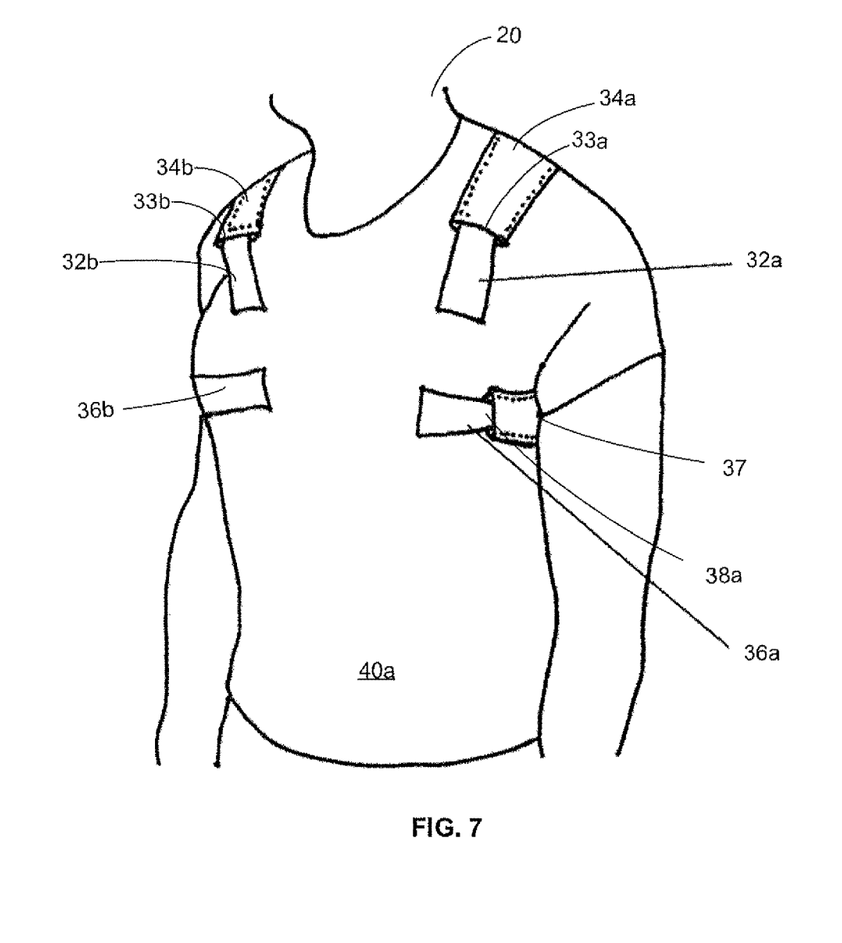
FIG. 7 shows the posture garment of FIG. 6A being worn by a user when the garment is in the retracted position.

In FIG. 6A, the straps 32a, 32b and 36 are enclosed in their respective sleeves 34a, 34b and 38 and are not visible. It is also evident that the attachment regions 42 and 46 are not holding straps 32a, 32b and 36 and therefore no tension is being applied by the elastic straps. However, in FIG. 6B, the posture garment 40 is in the retracted position and the end portions of the straps 32a, 32b and strap 36 are engaged or releasably attached to attachment regions 42 and 46. The straps 32a, 32b and 36 may be releasably attached to the attachment regions 42 and 46, respectively, using any suitable connector including, without limitation, Velcro™, D-Rings, snaps, connection clips, buttons, or any other suitable means for releasable connection. FIG. 7 shows the posture garment 40 being worn by a user 20 when the posture garment 40 is in the retracted position.

In another aspect, a method for making the posture garment 30 may comprise: forming front and rear garment portions 30a and 30b of the posture garment (such as by cutting the portions from a material using a pattern), anchoring first end portions of the upper straps 32a and 32b and a portion of the lower strap 36 to anchor points 31 and 39 near a midline region of the rear garment portion 30b, mounting the sleeves 33a, 33b and 37 over the straps 32a, 32b and 36, respectively, and attaching the sleeves 33a, 33b and 37 on the garment 30 while leaving openings 34a, 34b, 38a and 38c near the upper shoulder regions and beneath the armpit regions where the rear garment portion 30b will be attached to the front garment portion 30a and then attaching (such as by sewing) the front garment portion 30a and the rear garment portion 30b to one another. The end portions of the straps 32a, 32b and 36 that will be joined together or to a region of the garment to move the garment to the tensioned position during use will then be provided with attachment means as described previously such as Velcro™, for example.

The garments described in accordance with the teachings herein may be constructed in a variety of formats including, but not limited to, a shirt, a vest, bra, sports bra, tank top, brasserie and the like.

While the applicant's teachings described herein are in conjunction with various embodiments for illustrative purposes, it is not intended that the applicant's teachings be limited to such embodiments as these the embodiments described herein are intended to be examples. On the contrary, the applicant's teachings described and illustrated herein encompass various alternatives, modifications, and equivalents, without departing from the embodiments described herein, the general scope of which is defined in the appended claims.

REFERENCES

1. Bureau of Labor Statistics, (2008), "Nonfatal occupational injuries and illnesses requiring days away from work, 2007", Washington, D.C., U.S. Department of Labor, Retrieved on Mar. 1, 2009.
2. National Institute for Occupational Safety and Health (NIOSH), (2007), "Ergonomic guidelines for manual material handling", DHHS Publication No. 2007-131, Washington, D.C.: U.S. Department of Health and Human Services, Centers for Disease Control and Prevention, NIOSH.
3. Bureau of Labor Statistics, U.S. Department of Labor, (2001), "Lost-work time injuries and illnesses: characteristics and resulting days away from work. Available from: http://www.bls.gov/iif/oshwc/osh/case/ostb1177.pdf.
4. McGee, R., Bevan, S., & Quadrello, T., (2007), "Fit For Work? Musculoskeletal Disorders and the Canadian Labour Market. The Work Foundation.", available from: http://www.conferenceboard.ca/Libraries/NETWORK_PUBLIC/CCDPM_report2_jul2011.sflb.
5. Sundelin, G., Hagberg, M., Hammarstrom, U., (1986), "The effect of pauses on muscular load and perceived discomfort when working at a VDT word processor", In proceedings of the international scientific conference: Work with display units Part one, Stockholm, page 501-502.
6. Zwahlen, Helmut T. and Jr., Charles C. Adams, (1987), "Development of a Work-Rest Schedule for VDT Work", In: Salvendy, Gavriel, Sauter, Steven L. and Jr., Joseph J. Hurrell (eds.) Social, Ergonomic and Stress Aspects of Work with Computers, Proceedings of the Second International Conference on Human-Computer Interaction—Volume 1 Aug. 10-14, 1987, Honolulu, Hi. pp. 157-164. p. 165-172.
7. Swanson, N. G., S. L. Sauter, L. J. Chapman, (1989), «The design of rest breaks for video display terminal work: A review of the relevant literature", In Advances in Industrial Ergonomics and Safety New York: Taylor & Francis, pp. 895-898.
8. Carter J B, Banister E W., (1994), "Musculoskeletal problems in VDT work: a review", Ergonomics, 37(10): 1623-48.
9. Hales T R, Sauter S L, Peterson M R, Fine L J, Putz-Anderson V, Schleifer L R, et al., (1994), "Musculoskeletal disorders among visual display terminal users in a telecommunications company", Ergonomics, 37:1603-21.
10. Sundelin, G., Hagberg, M., (1989), "The effect of different pause types on neck and shoulder EMG activity during VDU work", Ergonomics, 32: 527-537.
11. Anderson, J A D, (1984), "Shoulder pain and tension neck and their relation to work", Scandinavian Journal Work Environment Health, 10:435-442.
12. Knudson, D., Magnusson, P. and McHugh, M., (2000), "Current issues in flexibility fitness", President's Council on Physical Fitness and Sports Research Digest, 3(9): 1-8.
13. Harvey, L., Herbert, R. and Crosbie, J., (2002), "Does stretching induce lasting increases in joint rom? A systematic review", Physiotherapy Research International, 7: 1-13.
14. Shrier, 1., (2004), "Does stretching improve performance? A systematic and clinical review of the literature", Clinical Journal of Sport Medicine, 14: 256-273.
15. Decoster, L. C., Cleland, J., Alfieri, C. and Russell, P., (2005), "The effects of hamstring stretching on range of motion: a systematic literature review", Journal of Orthopedic and Sports Physical Therapy, 35: 377-387.
16. Magnusson and Renstrom, (1998), "A biomechanical evaluation of cyclic and static stretch in human skeletal muscle", International Journal Sports Medicine; 19: 310-316.
17. Sharman, Melanie J., Andrew G. Cresswell, & Riek, S. (2006), "Proprioceptive neuromuscular facilitation stretching: Mechanisms and clinical implications", Sports Medicine, 36(11), 929-939.
18. Guissard, N. and Duchateau, J., (2004), "Effect of static stretch training on neural and mechanical properties of the human plantar-flexor muscles", Muscle & Nerve, 29: 248-255.
19. Galinsky, T., Swanson, N., Sauter, S., Dunkin, R., Hurrell, J., & Schleifer, L., (2007), "Supplementary breaks and stretching exercises for data entry operators: A follow-up field study", American Journal of Industrial Medicine, 50(7), 519-527.
20. Trujillo L, Zeng X., (2006), "Data entry workers perceptions and satisfaction response to the "stop and stretch" software program", Work, 27: 111-121.

The invention claimed is:

1. A garment for altering the posture of an individual, comprising:
an adjustable set of straps, encircling the back and shoulders of the individual, the straps have end portions which can be adjustably connected to one another at a front chest region of the individual wearing the garment, the adjustment of the straps allowing the tension of the straps to be varied to bias shoulders of the individual back and downward from a non-tensioned, rest position; and
sleeves that house the straps and have openings through which the end portions of the straps extend during use to apply tension to the shoulders of the individual and the end portions of the straps retract within the openings when the straps are in the rest position.

2. The garment of claim 1, wherein the sleeves comprise a series of loops, fastened to the garment, through which the straps are located.

3. The garment of claim 1, wherein the sleeves comprise fabric passages formed in the garment.

4. The garment of claim 1, wherein the straps are resilient.

5. A method for making a posture garment for improving an individual's posture when the individual wears the garment, wherein the method comprises:
forming front and rear garment portions of the posture garment;
anchoring first end portions of upper straps and a portion of a lower strap to anchor points near a midline region of the rear garment portion;
positioning the upper straps to extend from the rear garment portion above shoulder regions of the posture garment so that second end portions of the upper straps are disposed at the front garment portion;
positioning opposing portions of the lower strap to extend from the rear garment portion below armpit regions of the posture garment to the front garment portion so that end portions of the lower strap are disposed at the front garment portion,
mounting sleeves over the straps and attaching the sleeves on the posture garment while leaving openings near upper shoulder regions and beneath armpit regions where the rear garment portion will be attached to the front garment portion so that the upper and lower straps are adjustable from a rest position, where the straps are disengaged and no pulling force is applied to the garment wearer, to a tensioned position where the straps are engaged and a pulling force is applied to the garment wearer;
attaching the front garment portion and the rear garment portion to one another; and
providing the end portions of the straps with attachment means.

6. A garment for applying a passive stretch to an individual's upper body when the individual wears the garment, wherein the garment comprises:
a front garment portion to cover at least a front portion of the individual's torso;
a rear garment portion to cover at least a rear portion of the individual's torso, the rear garment portion being attached to the front garment portion; and
an adjustable strap mechanism that comprises a set of straps extending above shoulder regions and below armpit regions of the garment from the rear garment portion to the front garment portion, the adjustable strap mechanism being adjustable from a rest position, where the straps are disengaged and no pulling force is applied to the garment wearer, to a tensioned position where the straps are engaged and a pulling force is applied to the garment wearer.

7. The garment of claim 6, wherein the set of straps exert a downward retraction pulling force on the individual's shoulders and a backward pulling force on the individual's chest region when in the tensioned position.

8. The garment of claim 6, wherein the set of straps comprises anchored portions that are anchored to the rear garment portion and end portions that extend to the front garment portion.

9. The garment of claim 8, wherein the anchored portions of the straps are anchored on separate areas of the rear garment portion.

10. The garment of claim 6, wherein the straps are resilient.

11. The garment of claim 6, wherein each strap of the adjustable strap mechanism includes an end portion that extends to the front garment portion.

12. The garment of claim 11, wherein during use in the tensioned position, the end portions of the straps that extend over the shoulder regions are releasably coupled to the end portions of the straps that extend under the armpit regions and the releasably coupled end portions are disposed along an area of the front garment portion.

13. The garment of claim 11, wherein in the tensioned position, opposing end portions of the straps releasably couple to one another.

14. The garment of claim 11, wherein in the tensioned position, end portions of the straps that extend over the shoulder regions of the garment releasably couple to an upper region on the chest area of the front garment portion and the end portions of the strap that extend under the armpit regions releasably couple to a lower chest region on the front garment portion.

15. The garment of claim 11, wherein the end portions of the straps are at least one of thicker and wider when the individual has a larger torso.

16. The garment of claim 11, wherein the set of straps are housed within a set of sleeves and in the rest position end portions of the straps retract within the sleeves and in the tensioned position, the end portions of the straps engage one another or regions of the front garment portion.

17. The garment of claim 16, wherein the end portions of the straps retract within the respective openings in the front garment portion so as not to be visible but can still be gripped when the individual reaches into the openings in the front garment portion.

18. The garment of claim 16, wherein opposing end portions of the sleeves near the openings are angled so that the opposing end portions of the straps form an arc in the tensioned position.

19. The garment of claim 16, wherein a top set of the sleeves extend over the shoulder regions of the front and rear garment portions, are angled in a V pattern and meet at a mid-region of a lower sleeve that extends under the armpit regions of the front and rear garment portions.

20. The garment of claim 16, wherein a top set of the sleeves extend over the shoulder regions of the front and rear garment portions and approximately run vertically down to separate regions of a lower sleeve that extends under the armpit regions of the front and rear garment portions.

21. The garment of claim 16, wherein the sleeves are formed by continuous sheets of material.

22. The garment of claim 16, wherein the sleeves are formed by a series of loops.

* * * * *